United States Patent [19]

Kusanagi et al.

[11] Patent Number: 4,490,715
[45] Date of Patent: Dec. 25, 1984

[54] GAS DETECTOR

[75] Inventors: Shigekazu Kusanagi, Katano; Shigeo Akiyama, Kadoma; Tohru Nobutani, Osaka; Hideo Kawamura, Neyagawa, all of Japan

[73] Assignee: Matsushita Electric Works, Ltd., Osaka, Japan

[21] Appl. No.: 302,161

[22] Filed: Sep. 14, 1981

[30] Foreign Application Priority Data

Sep. 13, 1980 [JP] Japan ................................ 55-127764
Nov. 21, 1980 [JP] Japan ................................ 55-164891

[51] Int. Cl.$^3$ .............................................. G08B 17/10
[52] U.S. Cl. .................................... 340/634; 340/632; 73/27 R; 338/34
[58] Field of Search ................... 340/632, 634; 338/34; 73/23, 27 R; 422/98

[56] References Cited

U.S. PATENT DOCUMENTS

| | | | |
|---|---|---|---|
| 4,164,862 | 8/1979 | Jackson | 73/27 R |
| 4,219,806 | 8/1980 | Enemark | 340/632 |
| 4,250,829 | 2/1981 | Stephens, Jr. | 340/634 |
| 4,256,985 | 3/1981 | Goodson et al. | 340/634 |
| 4,258,563 | 3/1981 | Yasuda et al. | 338/34 |
| 4,345,242 | 8/1982 | Ienna-Balistreri | 340/634 |
| 4,352,087 | 9/1982 | Wittmaier | 340/632 |

Primary Examiner—Gerald L. Brigance

[57] ABSTRACT

A gas detector for detecting the leak of fuel gases, such as hydrogen gas, methane gas, butane gas, with improved reliability in detecting the gas leak. Said gas detector includes a main gas sensing element showing the change in resistance to target gases, such as methane, butane, hydrogen, as well as to non-target gases, such as alcohol, steam, smoke; an auxiliary gas sensing element showing change in resistance rather to non-target gas than to target gas; the first comparator receiving the output induced by resistance change in main gas sensor, as input; the second comparator with reference voltage set at lower level than that for the first comparator; and a gate circuit for blocking the alarm driving signal of the second comparator by the output induced by resistance change in auxiliary gas sensor. The output obtained from either said gate circuit or the first comparator is used for alarm driving signal of alarm circuit.

9 Claims, 3 Drawing Figures

GAS DETECTOR

BACKGROUND OF THE INVENTION

1. Field of the Invention

The present invention relates to a gas detector, and more particularly to a gas detector capable of giving a driving signal to an alarm for the leak of fuel gases, such as hydrogen gas, methane gas, butane gas, with high reliability, by eliminating the noise induced by steam, ethanol gas, or smoke, etc. present concurrently with said fuel gases.

2. Prior Art

Generally, metallic oxides, such as $SnO_2$, $ZnO$, $Fe_2O_3$, $In_2O_3$, $WO_2$, $CeO_2$, have the property of showing a resistance change when they come into contact with hydrogen gas, methane gas, butane gas, etc., while they are heated to high temperature, and by using such a property, they are applied to actual use as gas sensing elements for detecting the leak of fuel gases, including LPG and natural gas. However, said gas sensing elements are defective in selectivity to gases. That is, they show the resistance change not only to target gases for detection, such as hydrogen gas, methane gas, butane gas, contained in LPG, natural gas, etc. consumed domestically, but also to steam formed during cooking as well as ethanol gas from various seasonings. Therefore, said gas sensing elements detect these other than the leaked fuel gases to be detected, thereby reducing the reliability of detection.

The prior art relating to the present invention has been disclosed in U.S. Pat. Nos. 3,644,795, 3,835,529 and 3,732,519 That is, U.S. Pat. No. 3,644,795 discloses a structure, wherein highly strong gas detection elements are used which are obtained by adding silicon compound into gas sensor components including semiconductors of metallic oxide such as $SnO_2$, $ZnO$, $Fe_2O_3$, or $NiO$, $Cr_2O_3$, and the output induced by change in resistance of said elements is inputted to a buzzer. U.S. Pat. No. 3,835,529 discloses a method for preparing a gas sensing element composed of metallic oxide semiconductors, such as $SnO_2$, $ZnO$, $Fe_2O_3$, $TiO_2$, $Cr_2O_3$, $NiO$, $CoO$, through processes of mixing, forming, baking and installation of electrode. And in U.S. Pat. No. 3,732,519, a gas sensing element including a pair of electrodes and porous metallic oxides containing semiconductor wherein the metallic oxides contain the particles of $Al_2O_3$ and $SiO_2$, was disclosed. All of them are inventions depending on the selectivity of gas sensing elements.

SUMMARY OF THE INVENTION

The primary object of the present invention is to provide a new gas detector which gives the alarm signal by correctly detecting the target gas in the presence of non-target gas alone, as well as in concurrent presence of target and non-target gases, by using a gas sensing element showing a resistance change with high sensitivity only to non-target gas, together with a gas sensing element, i.e. so called a sensitivity-defective gas sensor, showing a resistance change to target gas contained in fuel gases, as well as to non-target gas that should be excluded from target gases.

Another object of the present invention is to provide a new gas detector which triggers the alarm signal by instantly detecting the target gas when the target gas is contained in the air and gets high in concentration coming close to the dangerous point, regardless of in presence or absence of non-target gas.

A further object of the present invention is to provide a gas detector including a pair (or pairs) of gas sensing elements different in type of target gases to which said gas sensing elements show the resistance change, and thereby solving the problem of possible miss in detecting the target gas.

A still further object of the present invention is to provide a gas detector including a pair (or pairs) of gas sensing elements different in type of non-target gases to which said gas sensing elements show the resistance change, and thereby eliminating the erroneous operation due to the presence of non-target gases.

The still further objects of the present invention should become apparent through understanding the embodiments according to the present invention, as well as from innovations achieved by the present invention which are set in claims.

DETAILED DESCRIPTION OF THE INVENTION

Figure 1:
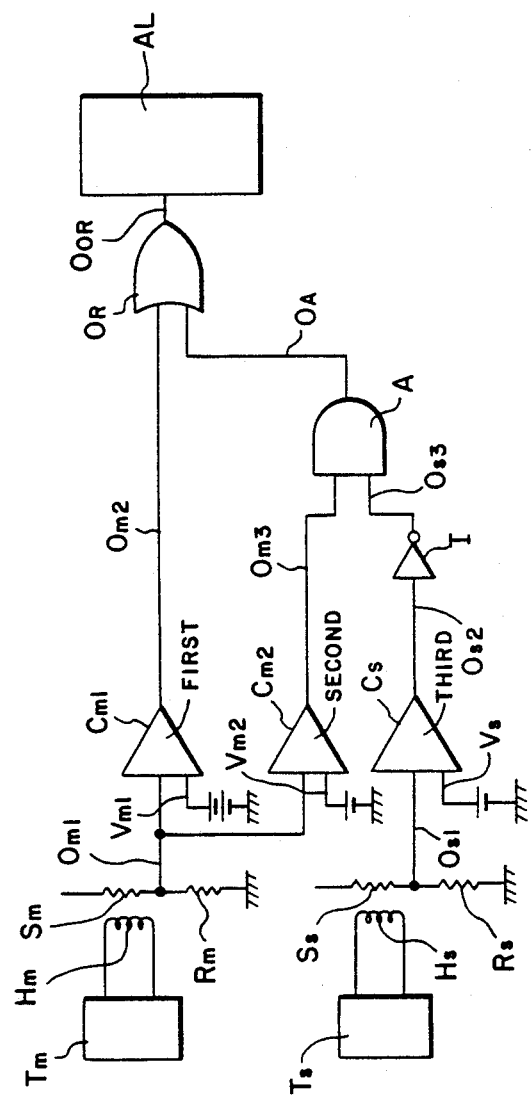
FIG. 1 is a basic circuit diagram of an embodiment according to the present invention.

FIG. 1 is a basic circuit diagram forming a gas detector according to the present invention, showing an embodiment, wherein metallic oxides with the property showing a decrease in electric resistance with increase in concentration of gases to be detected are used as the gas sensing element.

As shown in the figure, said embodiment includes a main gas sensing element (sensor) Sm showing a marked change in resistance by the contact of not only the target gases, but also the non-target gases; and an auxiliary gas sensing element Ss showing a greater change by the contact of non-target gases than by the contact of target gases. The main gas sensing element Sm and the auxiliary gas sensing element Ss are heated and maintained at the temperature where the marked resistance change occurs due to contact of respective gases. For said purpose, Sm and Ss include heaters Hm and Hs, respectively, and said heaters Hm and Hs are controlled to be kept at the element heating temperature where the resistance change rate shows its ultimate point, by temperature control circuits Tm and Ts provided with voltage circuits.

Prior to giving the description of the gas detection circuit, the description of the element will hereunder be given. As the main gas sensing elements shown in FIG. 1, metallic oxides, such as $SnO_2$, $ZnO$, $Fe_2O_3$, $WO_3$, $CeO_2$, $In_2O_3$, are used. Said metallic oxides are known to have the properties that they differ in resistance depending on the type of gases when the concentration of the gases is constant, and that, even when the gases are identical in type, said metallic oxides differ in resistance depending not only on the temperature at which they are maintained, but also on the concentration. Therefore, a specified resistance change caused when the concentration of leaking gas reaches to a specified point can be effected to produce a specified output through applying a specified voltage, and the detection signal can be obtained through comparing said output with reference voltage set up to be at specified level.

The description of the gas detection circuit will hereunder be given.

Said main gas sensing element Sm and its pairing counterpart, auxiliary gas sensing element Ss, are connected in series to resistors Rm and Rs, respectively. When the DC voltage is applied to both ends of the foregoing series circuits, the resistance changes of both the main gas sensing element Sm and auxiliary gas sensing element Ss are detected as both end voltages of each of resistors Rm and Rs, and the outputs Om 1 and Os 1 induced by those respective resistance changes are obtained. In other words, the main gas sensing element Sm and the auxiliary gas sensing element Ss make up the output circuit of gas sensing elements that obtains the outputs Om 1 and Os 1 induced by the resistance change caused by the contact with gas.

In said gas detection circuit, there are also the first comparator to which the output Om 1 induced by the resistance change in main gas sensing element Sm is received as input, and the second comparator Cm 2 disposed in parallel with said first comparator in a form making a pair with it are included. The reference voltage Vm 2 of said second comparator Cm 2 is set to be lower than the reference voltage Vm 1 of the first comparator Cm 1.

On the other hand, also the third comparator Cs to which the output Os 1 induced by the resistance change in auxiliary gas sensing element Ss is received as input, is included in said gas detection circuit. The reference voltage of said comparator Cs is set at Vs.

In addition, since the output Os 2 from the third comparator Cs comes from and is controlled by the auxiliary gas sensing element's specific property showing the increase of its electric resistance in parallel with increase in concentration of the gas to be detected, an inverter I for inverting said output Os 2 is provided. There is also an AND circuit A receiving the output Os 3 of said inverter I as well as the output Om 2 of the second comparator Cm 2 as inputs. Said AND circuit A forms a gate circuit for blocking the alarm actuating signal from the second comparator Cm 2 by means of the output Os 3 induced by the resistance change of auxiliary gas sensing element Ss.

Then there is an OR circuit Or for using either the output OA from the AND circuit A obtained based on the property of AND circuit A forming the gate circuit, or the output Om 2 from the first comparator Cm 1, as alarm actuating signal of an alarm circuit AL. By said alarm circuit AL a warning indication as to the gas detection is given. For expressing said warming, the widely known means, such as giving out an audible sound, emitting a visible light, are used without limit in type of the means.

Next, the description will be given on operation depending on the presence or absence of target and non-target gases which induce the resistance change in respective gas sensing elements Sm and Ss.

(1) In absence of both target and non-target gases no resistance change occurs in the main sensing element Sm as well as in the auxiliary gas sensing element Ss, including metallic oxides in which the electric resistance decreases with an increase in concentration of gas to be detected. Accordingly, the respective outputs Om 2, Om 3, Os 2, from the first comparator Cm 1, the second comparator Cm 2, and the third comparator Cs, which are set at the reference voltage higher than that of the outputs Om, Os 1, from respective elements can be obtained with L level. Then, although the L level output Os 2 obtained from the third comparator Cs is inversed in the inverter I to H level, in the AND circuit A that applies the logical product with L level output Om 3 obtained from the second comparator Cm 2, the output OA is obtained as L level output, and in the OR circuit Or where the logical sum of said output OA and L level output Om 2 from the first comparator Cm 1 is obtained in L level. By said L level output Or, the alarm circuit is not actuated. It means that the warming is not given when both the target and non-target gases are absent.

(2) In presence of detection target gases alone, in the auxiliary gas sensing element Ss, a slight decrease in resistance occurs in proportion to the concentration of the target gas, as a result of contact with said target gas, and in response to said decrease in resistance, the output Os 1 is obtained. The output Os 3 from the third comparator Cs with reference voltage set at higher level than that of said output Os 1 can be obtained with L level. Said L level output Os 2 is increased in the inverter I, and the output Os 2 is obtained in H level.

On the other hand, in the main gas sensing element Sm, a decrease in resistance proportional to the target gas concentration is caused, and in response to said resistance decrease, the output Om 1 is outputted. When said output Om 1 is higher in level than that of the reference voltage set in the second comparator Cm 2, the output Om 3 is obtained as a H level from the second comparator Cm 2.

Consequently, the inputs of the AND circuit A derived from the outputs Om 1, Os 1, from both the main gas sensing element Sm and the auxiliary gas sensing element Ss are of H level, therefore, from said AND circuit A, the H level output OA is obtained. Said H level output OA is processed in the OR circuit Or to obtain the logical sum with the L level output from the first comparator Cm 1, and the H level output Oor is result from said process in OR circuit Or, then, by said output Oor, the alarm circuit AL is actuated. It means that, in presence of the detection target gas alone, the target gas is detected.

When the output Om 1 induced by the contact with target gas with high concentration is higher in voltage level than the reference voltage of the first comparator Cm 1 where the reference voltage is set to be higher than that of the second comparator, from said first comparator Cm 1 the H level output Om 2 is obtained as an alarm actuating signal, without needing the use of the output from the second comparator for alarm driving signal.

(3) In presence of only the non-target gas, in the main gas sensing element, as a result of contact with a non-target gas, a decrease in the resistance occurs proportional to the concentration of said non-target gas, and in response to said decrease, the output Om 1 is obtained. When said output Om 1 is higher in level than that of the reference voltage Vm 2 of the second comparator Cm 2, the output of third comparator Cs is obtained at a H level.

At the same time the resistance of auxiliary gas sensing element Ss lowers, and according to said decrease, the output Os 1 is obtained. When said output Os 1 is higher in level than the reference voltage Vs of the third comparator Cs, the H level output Os 2 is obtained from the third comparator Cs. Said output Os 2 is inverted in the inverter I, and the L level output Os 3 is obtained. In the AND circuit A that takes the logical product of said L level output Os 3 with the output Om 3 from the second comparator Cm 2, the L level output Oa is obtained. In this case, because the output Om 2 from the first comparator Cm 1 is in L level, the L level output Oor is obtained in the OR circuit Or. In other words, the non-target gas is not detected, and the alarm circuit AL is not actuated.

However, even though the gas present is the non-target gas, when the output Om 1 with higher in level than the reference voltage Vm 1 is of the first comparator Cm 1 is obtained by the main gas sensing element Sm due to the presence of non-target gas with high concentration, Om 2 becomes high in level, causing the actuation of the alarm driving signal.

(4) In concurrent presence of non-target and target gases, the main gas sensing element Sm and the auxiliary gas sensing element Ss show a corresponding decrease the second comparator Cm 2 contains the output derived from the non-target gas as noise, the concentrations of the target gas in so extremely micro amount and thus unworthy to be detected does not apply to the detection failure.

When the output Om 1 from the main gas sensing element affected by summing-up effect corresponds to the gas concentration causing the output higher in level than the reference voltage Vm 1 of the first comparator Cm 1, the output Om 1 from the first comparator Cm 1, the output Om 1 from the first comparator is obtained in H level, and the alarm actuating signal is given regardless of the output Oa from the AND circuit A.

The following table shows the operations described above in relation to the presence or absence of the target and the non-target gases by which the resistance change in respective gas sensing element Sm, Ss, is induced as mentioned above, together with operations in some other example cases.

TABLE 1

|  | IN PRESENCE OF NON-TARGET GAS FOR DETECTION | | | IN PRESENCE OF DETECTION TARGET GAS ALONE | | NEITHER DETECTION TARGET |
| --- | --- | --- | --- | --- | --- | --- |
|  | TARGET GAS ABSENT | EXTREMELY MICRO AMOUNT OF TARGET GAS PRESENT | HIGHLY CONCENTRATED TARGET GAS PRESENT | DETECTION TARGET GAS/LOW CONCENTRATION PRESENT | DETECTION TARGET GAS/HIGH CONCENTRATION PRESENT | NOR NON-TARGET GAS ARE PRESENT |
| Om 2 | L | L | H | L | H | L |
| Om 3 | H | H | H | H | H | L |
| Os 2 | H | H | H | L | L | L |
| Os 3 | L | L | L | H | H | H |
| Oa | L | L | L | H | H | L |
| Oor | L | L | H | H | H | L |
| WARNING | NOT GIVEN | NOT GIVEN | GIVEN | GIVEN | GIVEN | NOT GIVEN | in resistance by getting affected by summed up concentrations of non-target and target gas, and according to the respective decreases, the outputs Om 1 and Os 1 are obtained.

First, when the output Os 1 is higher in level than the reference voltage of the third comparator Cs receiving the output Os 1 from the auxiliary gas sensing element Ss as input, the H level output Os 2 is obtained from the third comparator Cs and said output Os 2 is inverted to L level in the inverter I.

On the other hand, when the output Om 1 from the main gas sensing element Sm is induced by the target gas being present in so extremely micro amount that it is unworthy for detection, if said output Om 1 is lower in level than the reference voltage of the second comparator Cm 2, the output Om 3 from the second comparator Cm 2 is obtained as L level output.

As the result, from the AND circuit A receiving the L level output Os 3 and the L level Om 3 as inputs, the H level output is not obtained and the alarm actuating signal is not given. That is, if the alarm driving signal is given at this point, it falls in the range of an erroneous signal.

Figure 2:
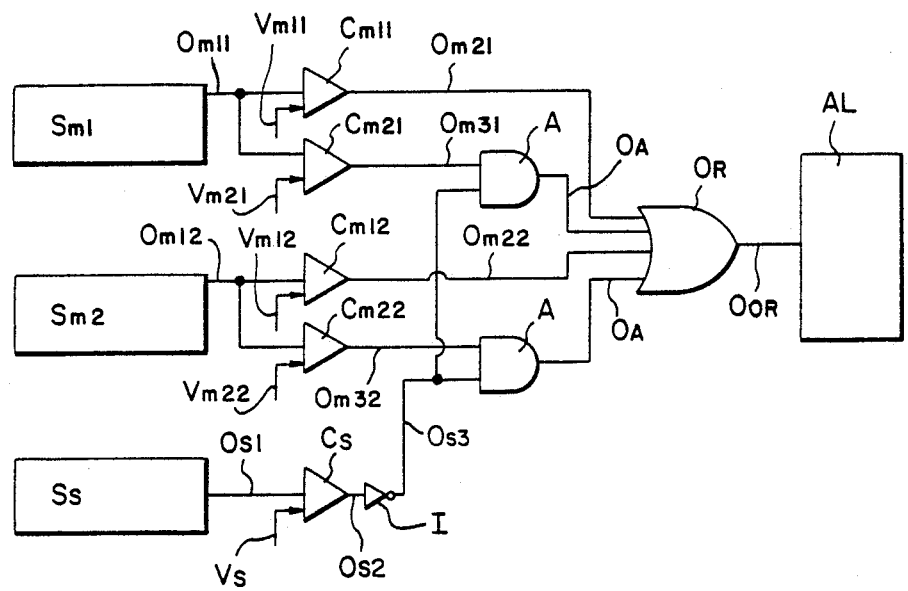
FIG. 2 is a circuit diagram showing a modification of the basic circuit according to this invention, shown in FIG. 1.

On the other hand, the output Om 1 of the main gas sensing element receiving the summed up effect of concentrations of target gas and non-target gas includes the output due to the non-target gas. Although, when the output Om 1 in this case reaches to the higher level than that of the reference voltage of the second comparator Cm 2, the output Om 3 of the second comparator Om 2 is obtained in a form of H level alarm actuating signal, it is blocked by the output from the auxiliary gas sensing element Os 3 inputted to the AND circuit which forms the gate circuit. However, since the output Om 3 from Next, the description will be given of FIG. 2. FIG. 2 is a gas detecting circuit diagram developed further from the basic circuit according to the present invention, that was shown in FIG. 1. The characteristic feature of the circuit diagram is the improved detection accuracy achieved through further relaxing the restriction in type of target gases, by the use of two types of main gas sensing elements which are different in properties. That is, it is an embodiment wherein two types of main gas sensing elements Sm 1, and Sm 2, differing in type of target gases to which the respective elements show the change in their resistance, are used, in order to relax the restriction on the type of target gases imposed due to the use of only one type of sensing element and thereby avoiding the possible miss in detection carried out by using the change in resistance shown by said gas sensing element to the target gas. As main gas sensing elements, following elements are provided in pairs: a main gas sensing element Sm 1 showing the more conspicuous change in resistance to, for example, hydrogen gas and butane gas, than to the other gases to be detected; and a main gas sensing element Sm 2 showing the more marked resistance to methane gas and propane gas, than to hydrogen gas and butane gas. Said main gas sensing elements are included in the output circuit for said elements. Said pairing main gas sensing elements Sm 1, Sm 2 have the property of showing the change in resistance to both target and non-target gases. Consequently, the output depending on the resistance change is brought about not only by the presence of the target gas, but also by the independent presence or concurrent presence of the non-target gas. From said gas sensing elements Sm 1, Sm 2, as was described with reference to FIG. 1A, the outputs Om 11, Om 12, due to the decrease in resistance are induced coinciding with said decrease in resistance caused by the contact with the above-mentioned gases. Also, the first comparators Cm 11, Cm 12, as well as the second comparators Cm 21, Cm 22, to which the outputs Om 11, Om 12, induced by the resistance change in said main gas sensing elements Sm 11, Sm 12, are inputted, are provided in each of the main gas sensing elements Sm1, Sm 2, respectively. The reference voltages Vm 21, Vm 22, of said second comparators Cm 21, Cm 22, are set at lower level than the reference voltages Vm 11, Vm 12, set for the first comparators Cm 11, Cm 12.

In addition, the third comparator Cs receiving the output Os 1 induced by the resistance change in auxiliary gas sensing element Ss as input is provided, and said comparator Cs is set at the reference voltage of Vs.

Furthermore, the output Os2 of the third comparator Cs is inverted in the inverter I, and the inverter output Os 3 is obtained. There are also provided the AND circuits A receiving the output Os 3 of said inverter I, as well as the putputs Om 21, Om 32, from the second comparators Cm 21, Cm 22, provided for each of pairing main gas sensing elements Sm 1, Sm 2, as inputs, and in said AND circuits A the outputs from inverter I and the second comparator Cm 21, Cm 22, are processed with logical product.

Then, there is the OR circuit Or receiving the outputs OA, OA, obtained from said AND circuits A, A, as well as the outputs Om 21, Om 22, from the first comparators Cm 11, Cm 12, provided respectively for the pairing main gas sensing elements as inputs. Said outputs are processed with logical sum in the OR circuit Or, Finally, there is the alarm circuit AL receiving the output Oor from the OR circuit Or as input. By said alarm circuit AL, the alarm is given as to the target gas.

The operations according to the presence or absence of the target and non-target gases inducing the resistance change in respective gas sensing elements in said embodiment should be apparent from the foregoing description.

Figure 3:
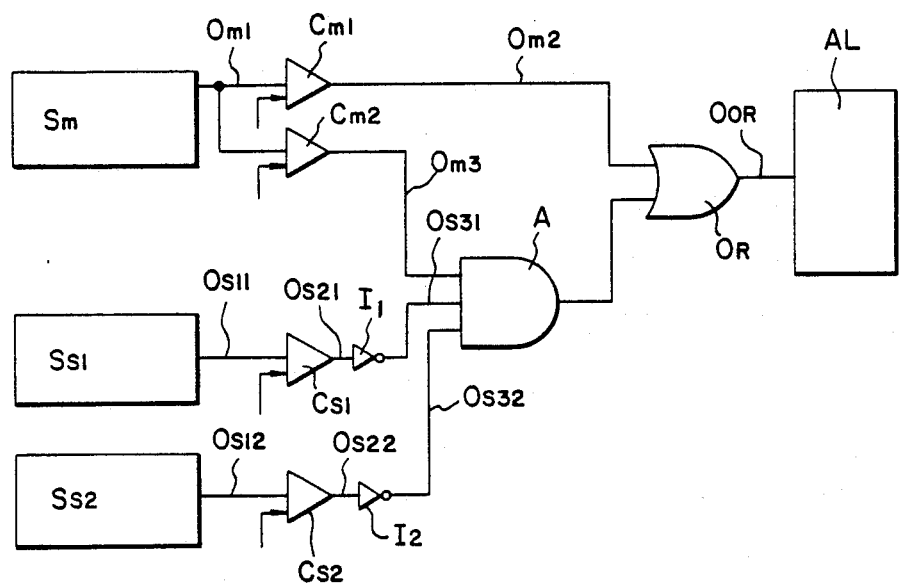
FIG. 3 is a circuit diagram showing another embodiment modified from the basic circuit according to this invention, shown in FIG. 1.

Finally, the description will be given on FIG. 3. Same as in FIG. 2, FIG. 3, is a gas detection circuit diagram developed further from the basic embodiment according to the present invention, shown in FIG. 1.

Said circuit diagram is an embodiment designed to avoid the errouneous detection signal induced by the resistance change shown by the main gas sensing element Sm with regard to the non-target gas; through provided two types of auxiliary gas sensing elements with different properties, thereby releasing the restriction imposed on the type of non-target gases because of the use of only one type of auxiliary gas sensing element. As auxiliary gas sensing elements, an auxiliary gas sensing element Ss 1 showing the more conspicuous change in resistance to, for example, ethanol gas, than to the other non-target gases, and an auxiliary gas sensing element Ss 2, showing the marked change in resistance only to smoke, different from said auxiliary gas sensing element Ss 1 are provided as a pair. Said respective elements are included in respective output circuits.

On the other hand, the main gas sensing element Sm has the property to show the change in resistance to both target and non-target gases. Therefore, the output from said main gas sensing element Sm due to resistance change is brought about not only by the presence of target gas, but also by the presence merely of non-target gas or the concurrent presence of non-target gas. For each of the comparators receiving the outputs Os 11, Os 12, from a pair of auxiliary gas sensing elements Ss 1, Ss 2, as inputs, the inverters I 1, I 2, are provided, and the outputs Os 21, Os 22, obtained from the comparators Cs 1, Cs 2, respectively, are inversed in the inverters I 1, I 2. The outputs Os 31, Os 32, obtained after inverted in the inverters I 1, I 2, and the output Om 3 from the second comparators Cm 2, receiving the output Om 1 from the main gas sensing element Sm as input, are inputted to the AND circuit A, and processed with logical product in said AND circuit A, for obtaining the output OA. The output OA obtained from said AND circuit A and the output Om 2 from the first comparator Cm 1 receiving the output Om 1 from the main gas sensing element Sm are inputted to the OR circuit Or, and processed here with logical sum.

Finally, there is the alarm circuit AL receiving the output Oor from the OR circuit OR as input is provided and by said alarm circuit AL, the warning as to the target gas is given.

The operations depending on the presence or absence of target and non-target gases inducing the resistance change in respective gas sensing elements should be apparent and are the same as those of the embodiment shown in FIG. 2. from the foregoing description given in reference to FIG. 1.

From the foregoing description, it should be apparent that the above-described embodiments are but a few of many possible specific embodiments, wherein 2 or more types of main gas sensing elements different in types of target gases to which they show the change in resistance are provided as a set, and also 2 or more types of auxiliary gas sensing elements differing in type of non-target gases to which they show the resistance change are provided in pairs, and numerous and varied other arrangements can be devised without departing from the spirit and scope of the invention.

A representative variation of the embodiment of this invention is that, wherein semiconductors of P form metallic oxides, such as molybdenum oxide, silicon oxide, are used as auxiliary gas sensing elements. It should be apparent from the foregoing description of the embodiments of this invention that, in the case mentioned above, because said P form metallic oxide semiconductors have the property to show the increase in resistance, in parallel with increase in gas concentration, the inverter shown in FIG. 1, FIG. 2, FIG. 3, where the N form metallic oxides are used as auxiliary gas sensing elements is unnecessary. Therefore, the present invention is not limited to the structure design described in detail in the above, and numerous and varied other arrangements can be devised without departing from the spirit and scope of the invention.

We claim:

1. A gas detector comprising:
a main signal processing unit, including a main gas sensing element showing a change in electric resistance value to both target and non-target gases and putting out a first alarm driving signal by detecting that the target and non-target gas exceeds a first specified level;
a sub-signal-processing unit including (1) a circuit unit to give a second alarm driving signal when the detected target and non-target gas exceeds a second specified level of concentration set lower than the first specified level, through the use of the main gas sensing element; and (2) a gate signal trigger unit for blocking the second alarm driving signal when the concentration of the non-target gas exceeds a third specified level, said gate signal trigger unit comprising an auxiliary gas sensing element showing a change in electric resistance in response to particularly non-target gas and a gate circuit unit coupled to the auxiliary gas sensing element; and an alarm triggering means that is actuated by receiving the first or second alarm driving signal.

2. A gas detector as set forth in claim 1, wherein:

the main signal processing unit includes a first comparator having a first reference voltage applied thereto and receiving a voltage varying depending on the resistance value of the main gas sensing element as an input; and said circuit unit to give the second alarm driving signal in said sub-signal-processing unit includes a second comparator having a second reference voltage lower than that of said first comparator, and receiving a voltage varying depending on the resistance value of the main gas sensing element as an input.

3. A gas detector as set forth in claim 1, wherein:

the gate signal giving unit includes a third comparator receiving a voltage varying depending on the resistance value of said auxiliary gas sensing element as input; and the gate circuit unit includes an AND circuit receiving an inversion signal of the third comparator as well as the second alarm driving signal as input.

4. A gas detector as set forth in claim 3, wherein the gate circuit unit includes an AND circuit receiving the output from the third comparator having the output from the auxiliary gas sensing element and the output from said second comparator as parallel inputs.

5. A gas detector as set forth in claim 1, wherein the main gas sensor includes at least 2 pairs of elements having different types of target gases to which they show resistance change.

6. A gas detector as set forth in claim 1, wherein the auxiliary gas sensor includes 2 or more types of pairing elements having different non-target gases to which they show the resistance charge, respectively.

7. A gas detector set forth in claim 1, wherein the main gas sensing element is a metallic oxide wherein a resistance thereof decreases with an increase in concentration of target gas.

8. A gas detector as set forth in claim 1, wherein the auxiliary gas sensing element is a metallic oxide wherein a resistance thereof decreases with an increase in conventration of non-target gas.

9. A gas detector as set forth in claim 1, wherein the auxiliary gas sensing element is a metallic oxide wherein a resistance thereof increases with an increase in concentration of non-target gas.

* * * * *